United States Patent
Ishino et al.

(10) Patent No.: US 9,840,700 B2
(45) Date of Patent: Dec. 12, 2017

(54) DNA CLEAVAGE ENZYME

(71) Applicant: Kyushu University, National University Corporation, Fukuoka (JP)

(72) Inventors: Yoshizumi Ishino, Fukuoka (JP); Sonoko Ishino, Fukuoka (JP); Miyako Shiraishi, Fukuoka (JP)

(73) Assignee: Kyushu University, National University Corporation, Fukuoka (JP)

( * ) Notice: Subject to any disclaimer, the term of this patent is extended or adjusted under 35 U.S.C. 154(b) by 0 days.

(21) Appl. No.: 14/890,009

(22) PCT Filed: May 9, 2014

(86) PCT No.: PCT/JP2014/062513
§ 371 (c)(1),
(2) Date: Nov. 9, 2015

(87) PCT Pub. No.: WO2014/181875
PCT Pub. Date: Nov. 13, 2014

(65) Prior Publication Data
US 2016/0304845 A1   Oct. 20, 2016

Related U.S. Application Data

(60) Provisional application No. 61/821,866, filed on May 10, 2013.

(51) Int. Cl.
*C12N 9/22* (2006.01)
*C12N 15/00* (2006.01)
*C12N 15/10* (2006.01)

(52) U.S. Cl.
CPC ............ *C12N 9/22* (2013.01); *C12N 15/102* (2013.01); *C12Y 301/00* (2013.01)

(58) Field of Classification Search
CPC .................................. C12N 9/22; C12N 15/00
USPC ........................... 530/350; 435/183, 6, 252.3
See application file for complete search history.

(56) References Cited

U.S. PATENT DOCUMENTS

2006/0248617 A1   11/2006   Imanaka et al.

FOREIGN PATENT DOCUMENTS

| EP | 1923464 A1 | 5/2008 |
|---|---|---|
| WO | 2004/022736 A1 | 3/2004 |

OTHER PUBLICATIONS

Communication issued Jun. 13, 2016, issued by the European Patent Office in counterpart European Patent Application No. 14794422.7.
Anonymous, "UPI00004A33AF", Jan. 1, 2005, XP 055274022, 2 pages total, http://www.uniprot.org/uniparc/UPI00004A33AF.
Cao, W., "Endonuclease V: an unusual enzyme for repair of DNA deamination", Cell and Molecular Life Sciences, Dec. 20, 2012, pp. 3145-3156, XP 002758108.
Anonymous, "UNIPROT: I6V2I0", Oct. 3, 2012, XP 055275861, 1 page total, http://ibis/exam/dbfetch.jsp?id=UNIPROT:I6V2I0.
(Continued)

*Primary Examiner* — Maryam Monshipouri
(74) *Attorney, Agent, or Firm* — Sughrue Mion, PLLC

(57) ABSTRACT

There is provided an enzyme which has an activity of cleaving a phosphodiester bond of deoxyribonucleotide having a damaged base and deoxyribonucleotide adjacent to the 5' side of the deoxyribonucleotide in DNA strands which contain the damaged base as a reagent or the like for manipulating a gene, and further provided a method of removing a damaged base from DNA strands using the enzyme.

23 Claims, 9 Drawing Sheets

(56) References Cited

OTHER PUBLICATIONS

Anonymous, "UNIPROT: Q8U0N5", Jun. 1, 2002, XP 055275876, 1 pages total, http://ibis/exam/dbfetch.jsp?id=UNIPROT:Q8U0N5.
"Pyrococcus furiosus DSM 3638, section 131 of 173 of the complete genome", GenBank: AE010256.1, Feb. 25, 2002, 5 pgs. total, http://www.ncbi.nlm.nih.gov/nuccore/AE010256.1?report=genbank.
Yong-jie Xu et al., "Excision of C-4*-oxidized Deoxyribose Lesions from Double-stranded DNA by Human Apurinic/Apyrimidinic Endonuclease (Ape1 Protein) and DNA Polymerase b*", The Journal of Biological Chemistry, vol. 273, No. 44, Oct. 30, 1998, 9 pgs. total.
Chia-Chia Lee et al. "Endonuclease V-mediated deoxyinosine excision repair in vitro", DNA Repair, vol. 9, 2010, pp. 1073-1079.
Arne Klungland et al., "Second pathway for completion of human DNA base excision-repair: reconstitution with purified proteins and requirement for DNase IV (FEN1)", The EMBO Journal, vol. 16 No. 11, 1997, pp. 3341-3348.
Miyako Shiraishi, "Archaea ni Miidasareta Sonsho Enki Shufuku Koso Endonuclease Q no Tokusei", Nippon Archaea Kekyukai Koenkai Yoshishu, vol. 26, Jul. 19, 2013, 2 pgs. total.
Int. Search Report dated Aug. 12, 2014 issued by the Int. Searching Authority in Application No. PCT/JP2014/062513 (PCT/ISA/210).
Written Opinion dated Aug. 12, 2014 issued by the Int. Searching Authority in Application No. PCT/JP2014/062513 (PCT/ISA/237).
Communication, dated Apr. 3, 2017, issued by the European Patent Office in counterpart European Application No. 14794422.7.
Communication, issued by the European Patent Office dated Sep. 20, 2017, in counterpart European Patent Application No. 14794422.7.

DNA CLEAVAGE ENZYME

TECHNICAL FIELD

The present invention relates to a DNA cleavage enzyme which is useful as a reagent for a gene in vitro, a method of producing the enzyme using a gene engineering technique, and a gene manipulation method using the enzyme.

BACKGROUND ART

With the development of molecular biology, the opportunity to perform gene (DNA) analysis has rapidly increased for various purposes. For this reason, in a gene manipulation technique of working on DNA strands or RNA strands in vitro according to the purpose, various enzymes having various activities are required. In addition, the current gene manipulation technique is not established without these enzymes.

In the gene engineering technique, various DNA-related enzymes have been used heretofore. As an enzyme that cleaves DNA, an enzyme that specifically recognizes a base sequence and cleaves DNA and an enzyme that recognizes a steric structure and cleaves DNA have been known. Among these, an enzyme, which is referred to as a restriction enzyme, has been frequently used as the enzyme that specifically recognizes a base sequence and cleaves DNA and generally recognizes 4 to 8 bases in a specific base sequence of a double-stranded DNA and cleaves the DNA. Meanwhile, as an enzyme that specifically cleaves a single-stranded DNA, an Si nuclease derived from *Aepergillus oryzae* which is an endonuclease that acts on a single-stranded DNA or an RNA to be decomposed into a mononucleotide; a P1 nuclease derived from *Penicillium citrinum*; and a Bal31 nuclease derived from *Alteromonas espejiana* are known and are commercially available.

In addition, in a case where a damaged base is present in DNA strands, Endonuclease V (Endo V) is known as an enzyme that recognizes the damaged base and specifically cleaves the 3' side of the damaged base (Non-Patent Document 1). In regard to Endonuclease V, for example, Endo V derived from *Escherichia coli* is commercially available as an enzyme for gene engineering (New England Biolabs, Ipswich, Mass., USA). Further, oxidative abasic damage caused by oxidative damage of deoxyribose in DNA strands is known and Endo IV derived from *Escherichia coli* or human abasic endonuclease (ApeI) is known as an enzyme involved in the cleavage (Non-Patent Document 2).

RELATED ART

Non-Patent Document

[Non-Patent Document 1] Cao W. (2012) Endonuclease V: an unusual enzyme for repair of DNA deamination. Cell Mol Life Sci. 2012 Dec. 20.

[Non-Patent Document 2] Yong-jie Xu, Edy Yong Kim, and Bruce Demple (1998) J Biol Chem. 1998 Oct. 30; 273 (44): 28837-44.

DISCLOSURE OF INVENTION

Problems to be Solved by the Invention

However, it is understood that lyase activity of MutM or DNA polymerase beta becomes necessary after cleavage of DNA strands by these enzymes and one nucleotide gap is generated after the cleavage (Non-Patent Document 2). That is, in regard to the endonuclease that recognizes a damaged base, an activity of directly cleaving a phosphodiester bond at the 5' side of the damaged base is not yet known and the presence of an enzyme having such an activity is unknown. However, if such an enzyme is present, since both ends of a damaged base are cut and the base can be removed by combining the enzyme and an enzyme (endonuclease V or the like) that cleaves the 3' side of the damaged base, it is expected that the enzyme will play a great role in developing a new gene engineering technology.

Accordingly, an object of the present invention is to provide an enzyme which has an activity of specifically and directly cleaving the 5' side of a damaged base in DNA strands which contain the damaged base as a reagent or the like for manipulating a gene and further provide a method of removing a damaged base from DNA strands using the enzyme.

Means for Solving the Problem

In view of the above-described problems, the present inventors focused on Endo V of *Pyrococcus furiosus* (hereinafter, referred to as *P. furiosus*) which is a kind of hyperthermophilic archaea (archaebacteria) and confirmed that this enzyme, similar to the known Endo V derived from *Escherichia coli* or other organisms, cleaves a phosphodiester bond of a nucleotide at the 3' side of a position in which hypoxanthine which is a damaged base generated by deamination of adenine in DNA strands is present.

In addition, as a result of extensive research which was further conducted, the present inventors found that a cell-extracted liquid of *P. furiosus* has an activity of providing a product whose 5' side of hypoxanthine is cleaved and performed identification of the protein causing the activity. The enzyme was identified as an enzyme that cleaves DNA strands having hypoxanthine as described above, and, thereafter, it was verified that the enzyme has an activity of cleaving DNA strands containing uracil or xanthine which is a damaged base or abasic DNA strands. Further, the present inventors succeeded in obtaining protein having homology to the protein from *Thermococcus kodakarensis* which is a related species with archaea and completed the present invention.

That is, the present invention relates to the following (1) to (19):

(1) An enzyme which has an activity of cleaving a phosphodiester bond of deoxyribonucleotide having a damaged base and deoxyribonucleotide adjacent to the 5' side of the deoxyribonucleotide in DNA strands which contain the damaged base.

(2) The enzyme described in (1) which has the amino acid sequence shown by SEQ ID NO: 2 or 4.

(3) The enzyme described in (1) which has the amino acid sequence shown by SEQ ID NO: 2 or 4 in which one or a plurality of amino acids are substituted with, deleted from, inserted into, and/or added to.

(4) The enzyme described in (1) which has an amino acid sequence having 95% or more homology to the amino acid sequence shown by SEQ ID NO: 2 or 4.

(5) The enzyme described in any one of (1) to (4), wherein the damaged base is hypoxanthine.

(6) The enzyme described in any one of (1) to (4), wherein the damaged base is xanthine.

(7) The enzyme described in any one of (1) to (4), wherein the damaged base is uracil.

(8) The enzyme described in any one of (1) to (4), wherein the damaged base is abasic.
(9) The enzyme described in any one of (1) to (8), which is derived from a family of Thermococcaceae.
(10) The enzyme described in (9), which is derived from the genus *Pyrococcus* or the genus *Thermococcus*.
(11) The enzyme described in (10), which is derived from *Pyrococcus furiosus* or *Thermococcus kodakarensis*.
(12) DNA which encodes the enzyme described in any one of (1) to (11).
(13) A recombinant vector containing the DNA described in (12).
(14) A transformant which is obtained by introducing the recombinant vector described in (13) to a host cell.
(15) A method of producing the enzyme described in any one of (1) to (11), comprising:
culturing the transformant described in (14) in a medium;
generating the enzyme described in any one of (1) to (11) and accumulating the same in a culture; and
collecting the enzyme from the culture.
(16) A method of removing a damaged base using the enzyme described in any one of (1) to (11) and Endo V.
(17) A method of removing a damaged base using the enzyme described in any one of (1) to (11) and a flap endonuclease.
(18) The method described in (16) or (17), wherein the damaged base is at least one selected from a group consisting of hypoxanthine, xanthine, uracil, and abasic.
(19) A gene manipulation method comprising:
removing a damaged base using the method described in any one of (16) to (18); and
ligating the cleaved portion through a DNA ligase reaction.

Effects of the Invention

The enzyme of the present invention has an activity of specifically recognizing abasic DNA strands resulting from a glycosidic bond between a base of DNA and saccharide being cut and hypoxanthine, xanthine, or uracil which is a damaged base resulting from adenine, guanine, and cytosine being respectively deaminated and cutting the DNA strands. Specifically, since the enzyme of the present invention is an entirely new enzyme showing specificity that directly cleaves the 5' side of a damaged base, the enzyme is expected to be applied to the development of a new gene engineering technology using these properties. Further, it is possible to provide a method of removing a damaged base from DNA strands by means of using the enzyme of the present invention.

EMBODIMENTS FOR CARRYING OUT THE INVENTION

Figure 1:
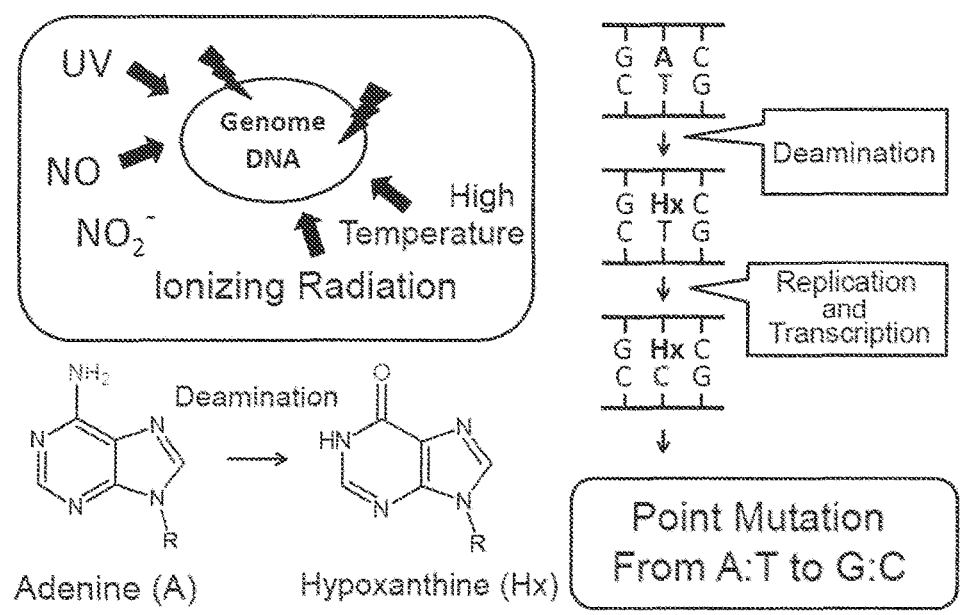
FIG. 1 is a view schematically illustrating deamination of a DNA base.

The display using abbreviations such as amino acid sequences and the like in the present specification will be made in conformity with the provision of IUPAC-IUB [IUPAc-IUB communication on Biological Nomenclature, Eur. J. Biochem., 138; 9 (1984)], "Guidelines for Preparation of Specification and the like with Base Sequence or Amino Acid Sequence" (Patent Office), and customary symbols in the related art.

(I) DNA of the Present Invention (Gene)

A gene of the present invention is a gene or a homolog thereof which is a gene PF1551 of *Pyrococcus. furiosus* and encodes a DNA cleavage enzyme (protein) having an activity of cleaving the 5' side of a damaged based in DNA.

That is, the gene of the present invention is a polynucleotide containing the following (a), (b), (c), (d), (e), (f), or (g).

(a) a polynucleotide which includes the base sequence shown by SEQ ID NO: 1;

(b) a polynucleotide which hybridizes with a polynucleotide including a base sequence complementary to the base sequence of the polynucleotide described in (a) under stringent conditions and encodes protein having a DNA cleavage activity of directly cleaving the 5' side of a damaged base in DNA;

(c) a polynucleotide which includes a base sequence in which one or a plurality of bases are substituted with, deleted from, inserted into, and/or added to in the base sequence of the polynucleotide described in (a) and encodes protein having a DNA decomposing activity of directly cleaving the 5' side of a damaged base in DNA;

(d) a polynucleotide which has at least 80% or more identity with the base sequence of the polynucleotide described in (a) and encodes protein having a DNA decomposing activity of directly cleaving the 5' side of a damaged base in DNA;

(e) a polynucleotide which encodes protein including the amino acid sequence shown by SEQ ID NO: 2;

(f) a polynucleotide which includes an amino acid sequence in which one or a plurality of amino acids are substituted with, deleted from, inserted into, and/or added to in the amino acid sequence of the protein described in (e) and encodes protein having a DNA decomposing activity of directly cleaving the 5' side of a damaged base in DNA; and (g) a polynucleotide which includes an amino acid sequence having at least 80% or more identity with the amino acid sequence of the protein described in (e) and encodes protein having a DNA decomposing activity of directly cleaving the 5' side of a damaged base in DNA.

Moreover, the gene of the present invention is a gene or a homolog thereof which is a gene TK0887 of *Thermococcus kodakarensis* which is archaea (archaebacteria) as a related species with *P. furiosus* and encodes protein having homology to the protein encoding PF1551.

That is, the gene of the present invention is a polynucleotide containing the following (h), (i), (j), (k), (l), (m), or (n).

(h) a polynucleotide which includes the base sequence shown by SEQ ID NO: 3;

(i) a polynucleotide which hybridizes with a polynucleotide including a base sequence complementary to the base sequence of the polynucleotide described in (h) under stringent conditions and encodes protein having a DNA cleavage activity of directly cleaving the 5' side of a damaged base in DNA;

(j) a polynucleotide which includes a base sequence in which one or a plurality of bases are substituted with, deleted from, inserted into, and/or added to in the base sequence of the polynucleotide described in (h) and encodes protein having a DNA decomposing activity of directly cleaving the 5' side of a damaged base in DNA;

(k) a polynucleotide which has at least 80% or more identity with the base sequence of the polynucleotide described in (h) and encodes protein having a DNA decomposing activity of directly cleaving the 5' side of a damaged base in DNA;

(l) a polynucleotide which encodes protein including the amino acid sequence shown by SEQ ID NO: 4;

(m) a polynucleotide which includes an amino acid sequence in which one or a plurality of amino acids are substituted with, deleted from, inserted into, and/or added to in the amino acid sequence of the protein described in (l) and encodes protein having a DNA decomposing activity of directly cleaving the 5' side of a damaged base in DNA; and (n) a polynucleotide which includes an amino acid sequence having at least 80% or more identity with the amino acid sequence of the protein described in (l) and encodes protein having a DNA decomposing activity of directly cleaving the 5' side of a damaged base in DNA.

In regard to the properties of protein or the enzyme in the present specification, unless otherwise specified, the expression "having a DNA cleavage activity of directly cleaving the 5' side of a damaged base in DNA" means having an activity of specifically recognizing at least one damaged base in DNA and cleaving a phosphodiester bond of deoxyribonucleotide having the damaged base and deoxyribonucleotide adjacent to the 5' side of the deoxyribonucleotide. A cleavage mode in which a phosphoric acid group remains in the 5' side and a hydroxyl group remains in the 3' side after cleavage is employed and ligation by a DNA ligase is possible.

The "damaged base" means a base which is damaged by DNA being exposed to a mutagen and, particularly in the present specification, means abasic DNA strands resulting from a glycosidic bond between a base of DNA and saccharide being cut due to a mutagen such as a high temperature, UV rays, ionizing radiation, or nitrous acid or a base deaminated by an amino group being deleted from and oxygen being bonded to (FIG. 1). Due to the deamination, adenine is changed into hypoxanthine, guanine is changed into xanthine, and cytosine is changed into uracil.

When a damaged base due to deamination remains unrepaired, for example, since hypoxanthine (Hx) makes a pair with cytosine (C), the base pair becomes (A:T→) Hx:T→Hx:C because of subsequent replication and transcription of DNA and then the base pair becomes Hx:C→G:C if replication is performed again. In this manner, A:T is point-mutated to G:C.

The "stringent conditions" indicate, unless otherwise specified, conditions of 6 M urea, 0.4% SDS, and 0.5×SSC or similar hybridization conditions and, in the present invention, more stringent conditions of 6 M urea, 0.4% SDS, and 0.1×SSC or similar hybridization conditions can be used as the stringent conditions as needed. In the respective conditions, the temperature can be set to approximately 40° C. or higher. In a case where more stringent conditions are required, the temperature may be set to approximately 50° C. or approximately 65° C.

In the present specification, in a case of "a base sequence in which one or a plurality of bases are substituted with, deleted from, inserted into, and/or added to," the number of nucleotides to be substituted or the like, which is not particularly limited as long as protein encoded by a polynucleotide including the base sequence has desired functions, is 1 to 9 or 1 to 4. Alternatively, in a case of substitution or the like that encodes amino acid sequences which are the same as each other or whose properties are similar to each other, greater numbers of substitutions or the like may be present.

Further, in the present specification, in a case of "an amino acid sequence in which one or a plurality of amino acids are substituted with, deleted from, inserted into, and/or added to," the number of amino acids to be substituted or the like, which is not particularly limited as long as protein including the amino acid sequence has desired functions, is 1 to 9 or 1 to 4. Alternatively, in a case of substitution or the like that constitutes protein which is the same as each other or whose properties are similar to each other, greater numbers of substitutions or the like may be present. Means for preparing a polynucleotide related to such a base sequence or an amino acid sequence are well known to those skilled in the art.

The gene of the present invention includes a base sequence having high identity with the base sequence shown by SEQ ID NO: 1 or 3 and contains a polynucleotide which encodes protein having a DNA cleavage activity that directly cleaves the 5' side of a damaged base in DNA.

Related to the base sequence, high identity indicates identity with at least 50% or greater, preferably 70% or greater, more preferably 80% or greater, still more preferably 90% or greater, and most preferably 95% or greater of the sequence. Further, the gene of the present invention includes an amino acid sequence having high identity with the entirety of the amino acid sequence shown by SEQ ID NO: 2 or 4 or at least a part having a portion from which a signal sequence is removed and contains a polynucleotide which encodes protein having a DNA decomposing activity. Related to the amino acid sequence, high identity indicates identity with at least 50% or greater, preferably 70% or greater, more preferably 80% or greater, still more preferably 90% or greater, and most preferably 95% or greater of the sequence.

The search and analysis for identity (also referred to as homology) between a polynucleotide sequence and an amino acid sequence can be performed by those skilled in the art using known algorithms or programs (for example, DNASIS software, BLAST, CLUSTAL W, and JALVIEW are used). Parameters at the time of using a program can be appropriately set by those skilled in the art and default parameters of respective programs may be used. Detailed procedures of these analysis methods are also known to those skilled in the art.

The polynucleotide of the present invention can be obtained from natural products using a hybridization technique, a polymerase chain reaction (PCR) technique, and the like. Specifically, genomic DNA (gDNA) is preferably prepared from prokaryotic microorganisms of *Thermococci* class, Thermococcales order, and Thermococcaceae family; more preferably from prokaryotic microorganisms of *Pyrococcus* class or *Thermococcus* class; still more preferably from prokaryotic microorganisms belonging to *Pyrococcus furiosus* or *Thermococcus kodakarensis*; and particularly preferably from *Pyrococcus furiosus* or all the RNAs are prepared from the aforementioned prokaryotic microorganisms to synthesize cDNA through reverse transcription. From gDNA or cDNA, a partial base sequence suitable for the DNA decomposition of the present invention is designed or used as a probe or a primer and the polynucleotide in a full length of the present invention can be obtained.

The polynucleotide of the present invention includes DNA and RNA, and the DNA includes genomic DNA, cDNA, and chemically synthesized DNA. The DNA may be a single-stranded DNA or a double-stranded DNA. The polynucleotide of the present invention may be derived from prokaryotic microorganisms belonging to *Pyrococcus* class or *Thermococcus* class; preferably from prokaryotic microorganisms belonging to *Pyrococcus furiosus* or *Thermococcus kodakarensis*; and more preferably from prokaryotic microorganisms of *Pyrococcus furiosus*. A base sequence derived from *Pyrococcus furiosus* is shown by SEQ ID NO: 1 of the sequence table and a base sequence derived from *Thermococcus kodakarensis* is shown by SEQ ID NO: 3 of the sequence table.

The present invention also provides a recombinant vector which contains the polynucleotide (the DNA of the present invention and the homolog thereof) according to the present invention and a transformant which is transformed by the recombinant vector. The present invention further provides a transformation method which includes a process of transforming a host (microbes or prokaryotic microorganisms, animal cells, or plant cells, for example, *Escherichia coli*) using the polynucleotide according to the present invention.

A vector to which the polynucleotide of the present invention is inserted is not particularly limited as long as the vector can express an insert in a host, and the vector normally includes a promoter sequence, a terminator sequence, a sequence for inductively expressing an insert using external stimulus, a sequence to be recognized by a restriction enzyme for inserting a target gene, and a sequence encoding a marker for selecting a transformant. In regard to the preparation of a recombinant vector and the transformation method using the recombinant vector, known methods can be applied by those skilled in the art.

(II) Enzyme of the Present Invention (Protein)

The enzyme of the present invention is protein or a homolog thereof to be encoded by PF 1551 which is the DNA of the present invention.

That is, the enzyme of the present invention is protein containing the following (e'), (f') or (g').

(e') protein which includes the amino acid sequence shown by SEQ ID NO: 2;

(f') protein which includes an amino acid sequence in which one or a plurality of amino acids are substituted with, deleted from, inserted into, and/or added to in the amino acid sequence of the protein described in (e') and has a DNA cleavage activity that directly cleaves the 5' side of a damaged base in DNA; and (g') protein which includes an amino acid sequence having at least 80% or greater identity with the amino acid sequence of the protein described in (e') and has a DNA cleavage activity that directly cleaves the 5' side of a damaged base in DNA.

Moreover, protein having homology to the protein which encodes PF1551 is also recognized in a gene TK0887 of *Thermococcus kodakarensis* which is archaea (archaebacteria) as a related species with *P. furiosus*.

Therefore, the enzyme of the present invention is a gene or a homolog that encodes protein having homology to the protein encoding TK0887.

That is, the enzyme of the present invention is protein containing the following (l'), (m'), or (n').

(l') protein which includes the amino acid sequence shown by SEQ ID NO: 4;

(m') protein which includes an amino acid sequence in which one or a plurality of amino acids are substituted with, deleted from, inserted into, and/or added to in the amino acid sequence of the protein described in (l') and has a DNA cleavage activity that directly cleaves the 5' side of a damaged base in DNA; and (n') protein which includes an amino acid sequence having at least 80% or greater identity with the amino acid sequence of the protein described in (l') and has a DNA cleavage activity that directly cleaves the 5' side of a damaged base in DNA.

The purification and the identification of the enzyme according to the present invention are performed as described below.

Figure 2:
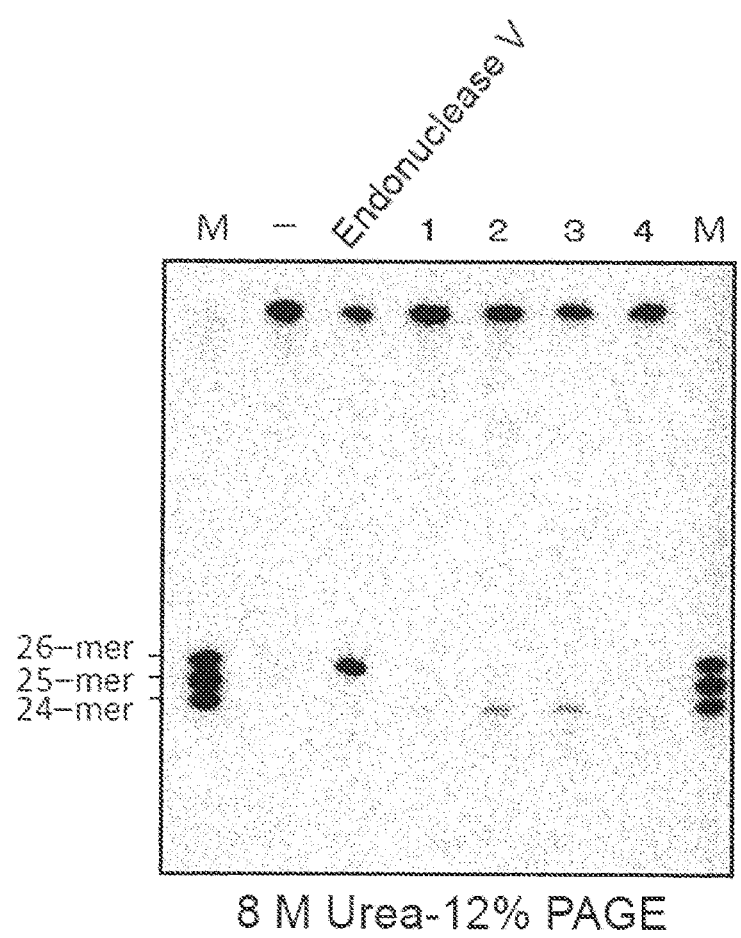
FIG. 2 is an electrophoregram showing results of screening of protein involved in excision repair of hypoxanthine which is contained in a cell-extracted liquid of *Pyrococcus furiosus*.

First, it is verified that a cell-extracted liquid of *Pyrococcus furiosus* has an activity of cleaving hypoxanthine-containing DNA which is a damaged base generated by adenine in DNA strands being deaminated. As a result of fractionating the cell-extracted liquid of *Pyrococcus furiosus* with cation exchange column chromatography and performing a cleavage reaction using hypoxanthine-containing and chemically synthesized DNA strands as a substrate with respective fractions, a fraction in which a band is detected at a position of 24mer is obtained in the sample Nos. 1 to 4 as shown in FIG. 2. Meanwhile, in a sample treated only by the purified "Endonuclease V," a band is detected at a position of 26mer. In the cleavage reaction caused by Endonuclease V, since it is understood that cleavage occurs on the downstream of one nucleotide at the 3' side of hypoxanthine, the appearance of the 24mer indicates that cleavage occurs at the 5' side of the hypoxanthine. Accordingly, the fractions of the sample Nos. 1 to 4 in which a band appears at the position of 24mer indicate that the cleavage activity occurs at the 5' side.

In addition, since it is verified that the fractions of the sample Nos. 1 to 4 contain Endonuclease V by western analysis, the cleavage reaction caused by Endonuclease V is expected to occur at the same time. Since labeling of DNA is made at the 5' terminal, shorter 24mer is only detected even when the cleavage reaction occurs at the same time.

Figure 4:
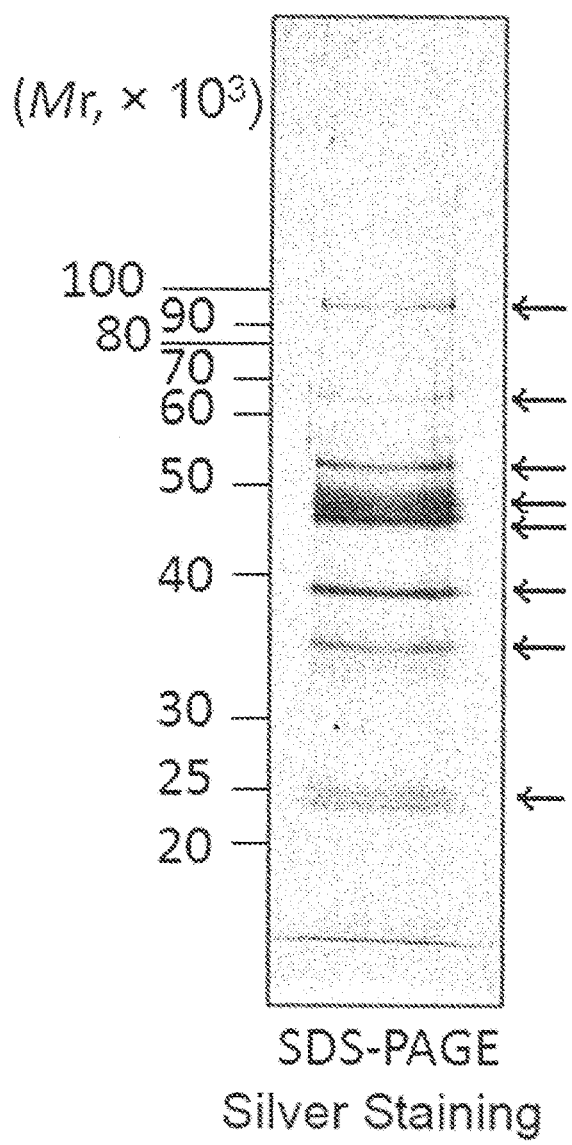
FIG. 4 is a diagram which shows results of electrophoresis of a final active fraction and in which protein contained therein is detected.

A target activity is concentrated by carefully fractionating a cell-extracted liquid of *P. furiosus* using five kinds of chromatographies whose principles are different from each other. When the fractions are supplied to SDS-PAGE and silver staining is performed, protein is detected as shown in FIG. 4. Eight bands indicated by arrows are cut out (Example 2 and FIG. 4) and subjected to high sensitivity mass analysis, and amino acid sequences of protein contained therein are acquired. As a result, twenty kinds of proteins are listed as candidates of proteins that provide the target activity.

Figure 5:
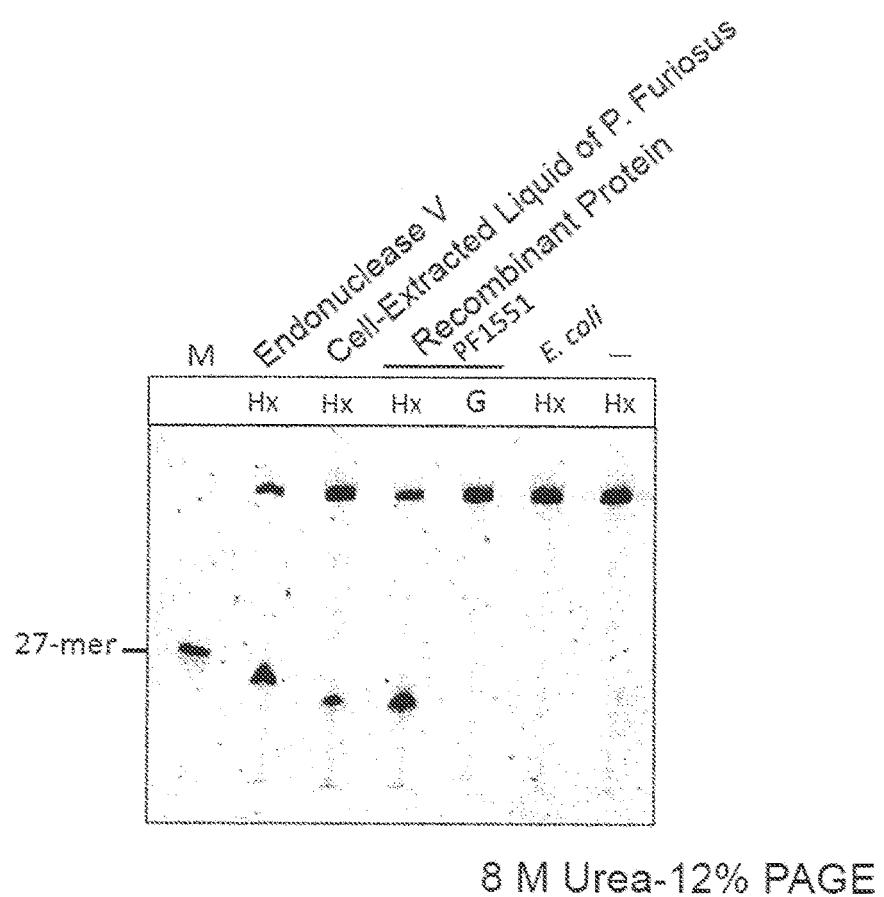
FIG. 5 is a diagram showing results of activity measurement of PF1551.

A gene encoding these proteins is cloned by genomic DNA of *P. furiosus* and is allowed to be expressed by *Escherichia coli*. When nuclease assay is performed using DNA containing a damaged base as a substrate with a cell-extracted liquid of obtained recombinant *Escherichia coli*, and an activity of providing a product at which the 5' side of a position in which a hypoxanthine base is present is detected similar to an activity detected from cells of *P. furiosus* is detected from one of the candidate proteins. Accordingly, it is understood that the protein having the activity is a product of the gene No. PF1551 of *P. furiosus* (FIG. 5).

This gene product is annotated as Hypothetical protein in a database and is protein having an unknown function. In the present invention, it is confirmed that the protein having an unknown function is an enzyme having a new activity of cleaving the 5' side of DNA strands which contain a hypoxanthine base. That is, it cannot be expected, from the sequences in the database, that an amino acid sequence obtained by translating a gene sequence has no homology to known proteins and is protein having such a nuclease activity specific to a damaged base.

Figure 6:
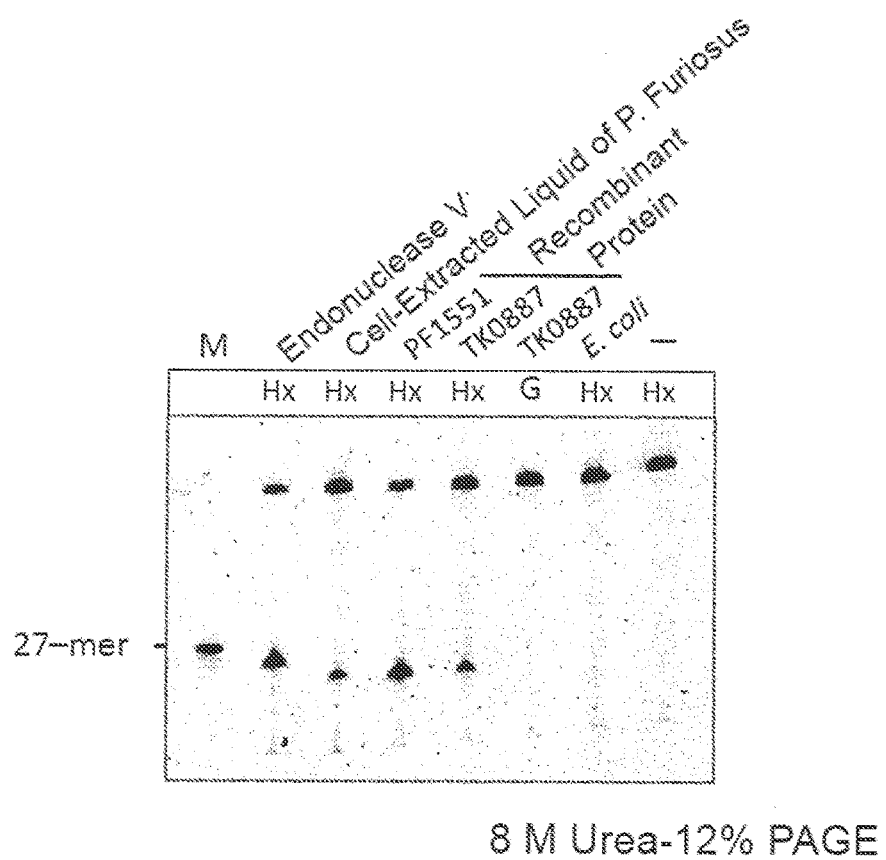
FIG. 6 is an electrophoregram showing results of activity measurement of PF1551 homolog (TK0887) derived from *Thermococcus kodakarensis*.

Moreover, the enzyme of the present invention is recognized in *Thermococcus kodakarensis*, the gene TK0887 is cloned, and recombinant *Escherichia coli* is prepared to express the gene. As a result of examining whether the gene product has the similar cleavage activity, an activity of providing a cleavage product which is the same as the case of PF1551 is detected even from the cell-extracted liquid as shown in FIG. 6. The cleavage activity is not detected in a DNA substrate which has G-T mismatch in which the portion of hypoxanthine (Hx) becomes G (lane G). Moreover, Hx is contained in the substrate of *Escherichia coli* that does not incorporate TK0887 genes, but cleavage does not occur therein (lane "*E. coli*").

The new DNA cleavage enzyme (protein which includes 424 amino acids shown by SEQ ID NO: 2 and has a molecular weight of 47,653) of the present invention is named Endonuclease Q (Endo Q). The enzyme is identified as an enzyme that cleaves DNA strands having hypoxanthine as described above. In order to research how stringent the substrate specificity is, as other damaged bases, when the DNA strands having hypoxanthine are cleaved and DNA strands containing uracil and xanthine, abasic DNA strands, and DNA containing mismatch base pairs are also subjected to the cleavage reaction according to the subsequent research, it is shown that DNA strands having uracil, xanthine, and an abasic portion are cleaved with the same efficiency.

Figure 7:
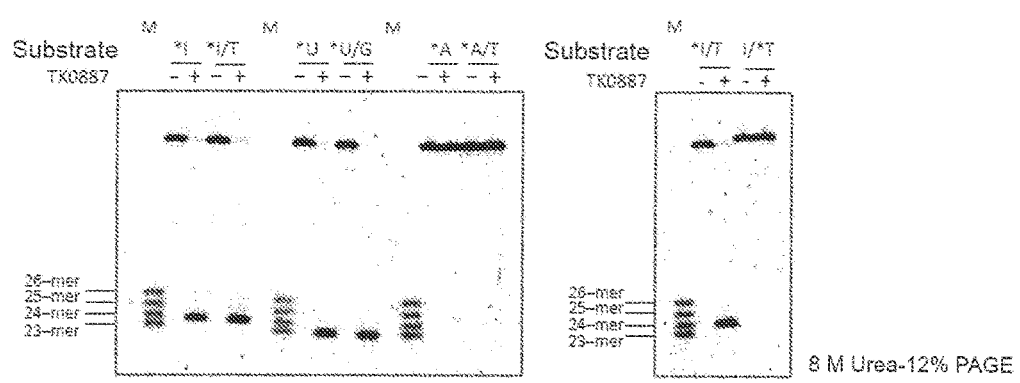
FIG. 7 is a diagram schematically showing a cleavage mode of Endo Q.
Figure 8:
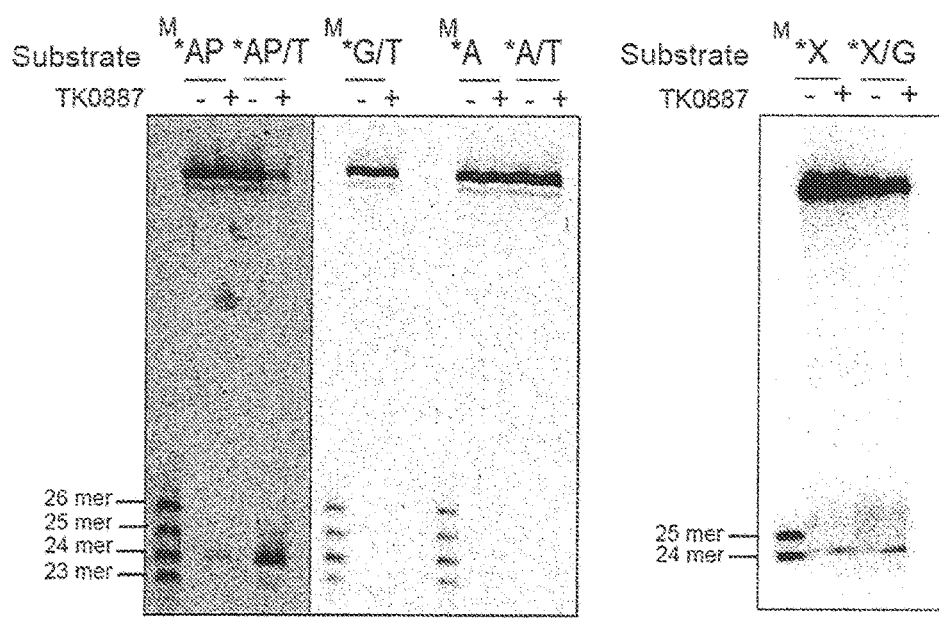
FIG. 8 is a diagram schematically showing a cleavage mode of Endo Q.

FIG. 7 shows a case of a DNA substrate containing hypoxanthine and a case of a DNA substrate containing uracil. In FIG. 7, *I, *U, and *A respectively indicate labeled single-stranded DNA substrates containing hypoxanthine, uracil, and adenine (normal DNA bases); and *I/T, *U/G, and *A/T respectively represent double-stranded DNA substrates having portions in which hypoxanthine, uracil, and adenine face thymine or guanine and *I/T, *U/G, and *A/T indicate that strands containing hypoxanthine, uracil, and adenine are labeled. Further, I/*T indicates a DNA substrate whose strand containing thymine in the double strands that include the portion in which hypoxanthine and thymine face each other is labeled. Further, FIG. 8 shows a case of using DNA strands respectively including an abasic portion, GT mismatch, and xanthine as a substrate. DNA substrates including an abasic portion and xanthine are cleaved at the same efficiency, but DNA substrates including normal double strands and GT mismatch are not cleaved at all. In FIG. 8, *AP, *A, and *X respectively indicate labeled single-stranded DNA substrates containing abasic, adenine, and xanthine; and *AP/T, *G/T, *A/T, and *X/G respectively represent double-stranded DNA substrates whose strands containing abasic, guanine, adenine, and xanthine in double-stranded DNA having a portion in which abasic, guanine, adenine, and xanthine face thymine or guanine are labeled.

In addition, the reason why the position of the band of a cleavage product is different from that in the case of hypoxanthine depending on the kind of a damaged base is that the position of a damaged base is different from the position of Hx due to the base sequence of the substrate DNA, but the cleavage position being the 5' side which is immediately next to the position of the damaged base does not change. In addition, as a result of carrying out a test by changing DNA strands to be labeled, a panel on the right side of FIG. 7 indicates that only the strand which includes hypoxanthine is cleaved and the DNA strand which does not include hypoxanthine is not cleaved in the case of the DNA substrate including hypoxanthine.

Figure 9:
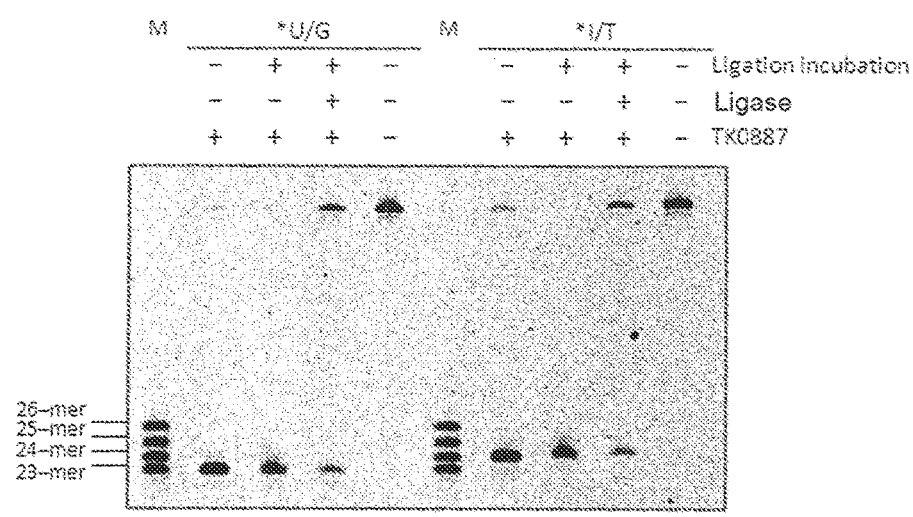
FIG. 9 is an electrophoregram showing ligation using a T4 ligase after cleavage by Endo Q.

Further, it is evidenced, by the results of the test shown in FIG. 9, that the DNA cleaved by the enzyme (Endo Q) of the present invention is cleaved such that the 5' side includes a phosphoric acid group and the 3' side includes a hydroxyl group as described above through ligation of the cleavage product using a T4 ligase.

Further, *P. furiosus* (DSM3638) is obtained from Deutsche Sammlung von Mikroorganismen und Zellkulturen GmbH (Inhoffenstrasse 7B 38124 Braunschweig GERMANY) and *T. kodakarensis* is obtained from the laboratory (Kyoto University Katsura, Saikyo-ku, Kyotoshi) in the biochemistry engineering field of the department of synthetic and biological chemistry of the Kyoto University Graduate School of engineering, thereby obtaining the protein of the present invention. In addition, *T. kodakarensis* (JCM 12380) can be obtained from Japan Collection of Microorganisms (microbial material development office, bioresource center, RIKEN, Incorporated Administrative Agency, 3-1-1, Takanodai, Tsukuba City, Ibaraki Prefecture).

A method of producing the enzyme (Endo Q) of the present invention is divided into the following processes.

(1) Process of Preparing Base Sequence that Encodes Enzyme having Amino Acid Sequence Shown by SEQ ID NO: 2 or 4.

A gene encoding the protein is extracted from a database of a genomic sequence and a primer for PCR is designed and chemically synthesized based on the gene sequences in both ends of a coding region. For example, PF1551-F (5'-GG GCC ATG GTA GTT GAT GGC GAT CTG CAC A-3', the restriction site of NcoI is underlined) (SEQ ID NO: 8) and the reverse primer PF1551-R (5'-GG GGC GGC CGC TTA ATT TAC CTC TTT ATT TTT AAT ATA TTG AAG C-3', the restriction site of NotI is underlined) (SEQ ID NO: 9) can be considered. The target gene is amplified in vitro under normal PCR conditions (50 μL reaction solution: 20 mM Tris-HCl, pH 8.0, 2 mM $MgCl_2$, 10 mM KCl, 10 mM $(NH_4)_2SO_4$, 0.1% TritonX-100, 0.1 mg/mL BSA containing 80 ng *P. furiosus* genomic DNA, 400 nM of respective primers, 200 μM of respective dNTPs, 2.5 units PfuDNA polymerase) using this primer set.

(2) Process of Inserting Base Sequence into Expression Vector to Obtain Recombinant Vector In a case where pET21d (+) which is an expression vector for *Escherichia coli* is used, when the primer sequence respectively includes recognition sequences of restriction enzymes NcoI and NotI and PCR amplified genes are treated by both enzymes, respective recognition sequences appear at both terminals. Accordingly, pET21d (+) is cleaved by NcoI and NotI in the same manner as that described above, the genes are inserted into the cleaved position, and then a recombinant vector can be obtained.

(3) Process of Transforming Host Cells Using Vector to Obtain Transformant

For example, in a case where *Escherichia coli* are used for a host and the transformation method is established. As the easiest way, foreign DNA is easily brought in a cell by immersing cells of *Escherichia coli* in a calcium chloride solution to stand still in ice. When a recombinant DNA solution prepared in vitro is added to the solution of cells, the host cells are transformed by the DNA and a transformant is obtained. In a case where pET21d (+) is used as a vector, *E. coli* BL21 CodonPlus (DE3)-RIL strains are suitable as the host cells.

(4) Process of Culturing Transformant

In a case where *E. coli* BL21 CodonPlus (DE3)-RIL strains to which the genes are introduced are cultured, shaking culture is performed at a temperature of 37° C. on an LB culture medium containing 50 µl/ml of ampicillin and 34 µl/ml of chloramphenicol, isopropyl 13-D thiogalactopyranoside (IPTG) is added such that the amount thereof becomes 1 mM when the turbidity $OD_{600}$ measured at a wavelength of 600 nm is grown to approximately 0.6, the mixture is subjected to induction of expression of the genes, and shaking culture is continued at 37° C. for 4 hours, thereby efficiently producing target protein.

(5) Process of Collecting Enzyme from Culture Solution

*Escherichia coli* which is cultured in the above-described manner is collected by centrifugation (4° C., 5,000×g, 5 minutes) and the cells are crushed using an ultrasonic crusher, thereby obtaining a cell-extracted liquid. The target protein has heat resistance, but host *Escherichia coli* is a room temperature organism and the protein thereof does not have heat resistance. Therefore, when the cell-extracted liquid is subjected to a heat treatment (for example, 80° C., 20 minutes), since most of the protein of the host is denatured and insolubilized, the modified and insolubilized part can be removed by centrifugation (4° C., 15,000×g, 10 minutes). Thereafter, target protein purified with a high purity can be prepared by continuing chromatographies whose principles are different from each other.

(III) Method of Removing Damaged Base of the Present Invention

The method of removing the damaged base of the present invention is a method of cutting out and removing a damaged base by combining the enzyme (endonuclease Q) of the present invention and Endo V or a flap endonuclease that cleaves a phosphodiester bond of a nucleotide at the 3' side of the damaged base.

After the damaged base is removed, the interface after cleavage can be ligated by carrying out a DNA ligase reaction.

EXAMPLES

The protein of the present invention can be easily prepared by those skilled in the art using a known method in the field based on the method in Examples described below and sequence information disclosed in the specification. Further, protein which includes a sequence obtained by modifying the sequence disclosed in the specification of the present application can be easily prepared by those skilled in the art using a known method in the field.

Further, the present invention is not limited by Examples described below.

Example 1

Identification of Cleavage Enzyme of the Invention of the Present Application

<Culture of *P. furiosus*>

After 1,000 mL of a culture medium containing 20 g of Bacto Trypton (BD), 5 g of Bacto Yeast Extract (BD), 23.9 g of sodium chloride, 10.8 g of magnesium chloride hexahydrate, 4 g of sodium sulfate, 10 g of Soluble Starch (DIFCO), and 10 mL of 100×trace element (30% $MgSO_4$, 10% NaCl, 1% $FeSO_4$.$7H_2O$, 1% $ZnSO_4$, 1% $CuSO_4$.$7H_2O$, 1% $CoSO_4$.$5H_2O$, 0.1% $CuSO_4$.$5H_2O$, 0.1% $KARSO_4)_2$, 0.1% $H_3BO_2$, $Na_2MoO_4$.$2H_2O$, 0.25% $NiCl_2$.$6H_2O$, pH 7.0) was autoclaved, a culture medium bottle was taken out when the inner temperature was decreased to 100° C., and then the inoculum of 2 mL of *P. furiosus* was added thereto. Subsequently, static culture was carried out at 98° C. The culture medium was taken out from an incubator when $OD_{600}$ became 0.6 and the culture solution was cooled with water for 10 minutes. Next, the culture solution was collected by centrifugation (4° C., 6,268×g, 10 minutes). The number of cells in the culture medium was calculated using a hemocytometer.

<Preparation of Cell-Extracted Liquid and Fractionation by column Chromatography>

The collected cells were suspended in 15 mL of a solution A (50 mM Tris-HCl, pH 8.0, 0.5 mM, DTT, 0.1 mM EDTA, 10% glycerol) in which complete mini EDTA-free (Roche) serving as a protease inhibitor were dissolved and sonication (5 seconds when turned on and 10 seconds when turned off, 10 minutes of total operating time) was carried out on ice. A supernatant obtained by performing centrifugation (4° C., 23,708×g, 10 minutes) on a sonication solution was set as a cell-extracted liquid. The cell-extracted liquid was dialyzed (4° C., 14 hours) by a solution B (10 mM potassium phosphate, pH 7.4) containing 0.1 M sodium chloride. The dialyzed liquid was provided for a phosphocellulose (P11) column equilibrated with the same solution, and the bound protein was fractionated by a linear concentration gradient of 0.1 M to 1 M NaCl. The target activity was eluted with 0.20 M to 0.37 M NaCl.

The fraction was dialyzed by a solution A containing 0.1 M NaCl and the dialyzed fraction was provided for a 1 mL HiTrap SP HP column (GE Healthcare). When the bound protein was eluted with a linear concentration gradient of 0.1 M to 1 M NaCl, the target activity was eluted in a position of 0.21 M to 0.41 M NaCl.

The fraction was diluted in the solution A and the NaCl concentration was decreased to 0.1 M or less. Further, the diluted fraction was provided for a 1 mL HiTrap Heparin HP column (GE Healthcare), the bound protein was fractionated with a concentration gradient of 0.1 M to 1 M NaCl, and the target activity was eluted in 0.27 M to 0.46 M NaCl.

The fraction was dialyzed by the solution B, and the dialyzed fraction was provided for a 1 mL hydroxyapatite column (ECONOPACK CHT-II; BIO-Rad). The bound protein was eluted with a concentration gradient (in the solution B) of 0.01 M to 0.5 M potassium phosphate and the target activity was obtained in a position of 0.23 M to 0.26 M potassium phosphate.

The fraction was provided for a 1 mL MonoS HR 5/5 column (Pharmacia). As a result of eluting the bound protein with a linear concentration gradient of 0 M to 0.3 M NaCl (in the solution A), a fraction having the target cleavage activity was obtained as shown in FIG. 3 and the fraction eluted in 0.23 M NaCl showed the highest activity.

Figure 3:
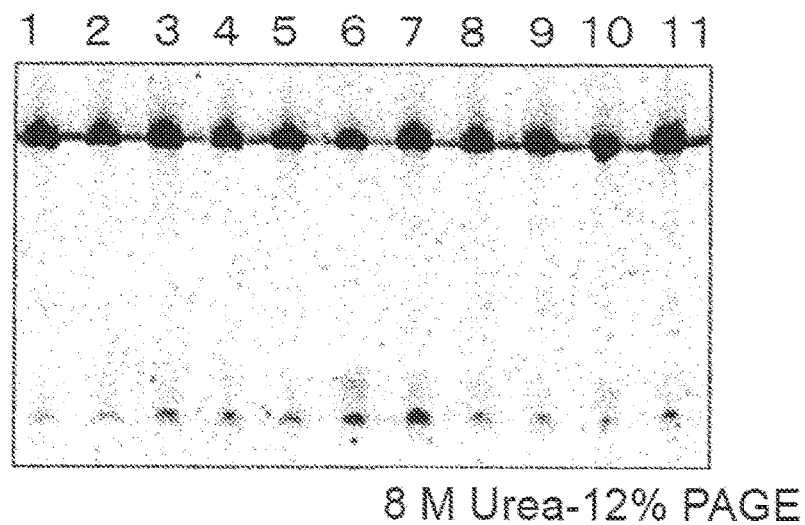
FIG. 3 is a diagram showing results of SDS-polyacrylamide gel electrophoresis of an active fraction.

According to FIG. 3, since it was expected that the fractions of the lanes 6 and 7 had the most target activity, the fraction of the lane 6 was provided for SDS-polyacrylamide gel electrophoresis and thus the protein contained in the fraction was detected by silver staining. As a result, as shown in FIG. 4, it was understood that various kinds of proteins were contained in the fraction. Among these, when clearly visible eight bonds (bonds shown by arrows in FIG. 4) were cut out and the respective bonds were subjected to high sensitivity mass analysis, twenty kinds of candidate proteins were listed up as the candidates of proteins that impart the target activity from viewpoints of linkage between the intensity of the activity and the band intensity, the presence or absence of a domain to be expected to be associated with the activity, the presence or absence of storage between archaea, and the presence or absence of annotations. That is, the candidate proteins were narrowed down through the processes, for example, other fractions were subjected to electrophoresis, proteins were detected by silver staining, the relative relationship between the density of a band and the intensity of the activity (band intensity of a cleavage product) shown in FIG. 3 was examined, the presence of a structure (sequence) to be expected as protein having the same word action as DNA was examined, the period for which the protein was stored between archaea was examined (in a case of important molecules, the degree of storage becomes higher), or the name of protein (for example, "DNA binding protein") whose function was expected on the database and on which annotation was performed was listed up.

Genes encoding twenty kinds of candidate proteins were cloned by genomic DNA of *P. furiosus* and the respective genes were expressed in *Escherichia coli*. In order to research the activity of respective gene products produced in cytoplasm, recombinant *Escherichia coli* cells were cultured and collected, and *Escherichia coli* cells were crushed using an ultrasonic cell crusher (astrason ultrasonic processor, Misonix Inc.) and centrifuged (4° C., 15,000×g, 10 minutes), thereby obtaining a cell-extracted liquid as a centrifuged supernatant. Further, the obtained liquid was treated in a hot water bath at 80° C. for 20 minutes and protein derived from host *Escherichia coli* was modified and removed by centrifugation (4° C., 15,000×g, 10 minutes), thereby obtaining a target fraction sample.

<Measurement of Endonuclease Activity>

Oligonucleotide whose 5' terminal was fluorescently labeled with Cy5, which contained hypoxanthine (25nt-th position from the 5' terminal), and whose chain length was 45 (Cy5-45N-d125) and oligonucleotide including a non-labeled complementary sequence and having a chain length of 45 (temp45N-normal) were mixed with each other in 30 µL of a TAM buffer solution (40 mM Tris-acetate (pH 7.8), 0.5 mM magnesium acetate) such that the final concentrations became respectively 500 nM and 750 nM and the solution was gradually cooled to 30° C. from 98° C. (using a PCR device), thereby preparing a double-stranded DNA substrate containing hypoxanthine (Hx-dsDNA).

Further, for the purpose of preparing a DNA substrate with no damaged base, normal DNA strands (45 N) in which the portion of hypoxanthine became adenine were prepared by being annealed under the same conditions as those of temp45N-normal. The base sequences of used oligonucleotides are as follows.

Cy5-45N-d125:
(SEQ ID NO: 5)
5'-cgaactgcctggaatcctgacgacitgtagegaacgatcacctca-
3' temp45N-normal:
(SEQ ID NO: 6)
5'-tgaggtgatcgttcgctacatgtcgtcaggattccaggcagttcg-
3'

45N:
(SEQ ID NO: 7)
5'-cgaactgcctggaatcctgacgacatgtagcgaacgatcacctca-
3'

20 µL of a reaction solution (10 nM Hx-dsDNA, 50 mM Tris-HCl (pH 8.0), 1 mM DTT, 0.1% Tween20, 1 mM MgCl$_2$, and 2 µL of fraction sample) was prepared and then reacted at 60° C. for 1 hour. After the reaction, 40 µL of a reaction stop solution (98% formamide, 10 mM EDTA, 0.1% Orange G) was added to the reaction solution to stop the reaction, and the solution was subjected to a heat treatment at 98° C. for 3 minutes and then rapidly cooled. 1.5 µL of the reaction solution was provided for 8M urea-12% polyacrylamide gel and the mixture was subjected to electrophoresis in 1×Tris-borate EDTA (TBE) (89 mM Tris, 89 mM boric acid, and 2 mM EDTA) at 20 W for 50 minutes. After the electrophoresis, DNA in the reaction solution was visualized using a Typhoon Trio+ (GE Healthcare image analyzer).

An activity, similar to the activity detected from cells of *P. furiosus*, imparting a product whose 5' side of a position, in which a hypoxanthine base was present, was cleaved was detected from recombinant *Escherichia coli* having the gene No. PF1551 from among candidate genes by cloning respective candidate protein genes obtained by mass analysis to prepare recombinant *Escherichia coli* and examining the activity thereof. Accordingly, it was understood that protein having the activity was a product having the gene No. PF1551 of *P. furiosus* (FIG. 5).

Example 2

In order to confirm whether a DNA terminal cleaved by the enzyme (Endo Q) of the present invention can be ligated using a DNA ligase which is a ligase of DNA strands, DNA (SEQ ID NO: 5) containing deoxyinosine and a DNA substrate in which C at the 5' side right next to the DNA was changed into U were annealed with DNA strands shown by SEQ ID NO: 6 and a double strand was formed. The double strand was reacted with TkoEndoQ (10 nM) in a reaction solution containing 50 mM Tris-HCl, pH 8.0, 1 mM DTT, 1 mM MgCl$_2$, and 0.01% Tween 20 at 75° C. for 20 minutes, the solution was allowed to stand still at 98° C. for 10 minutes, and then the enzyme was inactivated. Subsequently, the DNA was returned to a double strand by decreasing the temperature from 98° C. to 25° C. for 2 hours and a ligation reaction was carried out at room temperature for 30 minutes using Quick Ligation Kit (manufactured by New England Biolabs). The double strand was placed at 98° C. for 5 minutes and immediately moved into ice so as to be cooled. The sample was provided for 12% PAGE containing 8M urea and the electrophoretic image was visualized using a fluorescence image analyzer (Typhoon Trio+, manufactured by GE Healthcare) (FIG. 9). It was shown that 23mer (in a case of U) and 24mer (in a case of 1) serving as cleavage products was returned to have the original length (45mer) by adding a DNA ligase thereto.

As a result, it was confirmed that the cleaved DNA was ligated by the enzyme (Endo Q) of the present invention using a T4 ligase (FIG. 9).

The present invention has been described in detail with reference to particular embodiments, but it is apparent to those skilled in the art that various changes and modifications are possible within the range not departing from the spirit and the scope of the present invention. The present application is based on U.S. Provisional Application (61/

821,866) filed on May 10, 2013, the entire contents of which are incorporated herein by reference.

INDUSTRIAL APPLICABILITY

For example, the enzyme of the present invention can be applied to development of a detection kit that detects the frequency of DNA in cells to be damaged by various external factors and internal factors and a technique of only cleaving damaged DNA to be removed from a PCR mold and decreasing the mutation rate at the time of PCR to be generated due to the damage. Further, the enzyme of the present invention is hyperthermophilic because the enzyme is derived from hyperthermophile and is excellent in operability because the enzyme has remarkably excellent thermal stability. Therefore, the enzyme of the present invention is expected to be applied to development of a new technique as an enzyme for gene engineering being used in various gene engineering techniques.

The invention claimed is:

1. An enzyme which has an activity of cleaving a phosphodiester bond of deoxyribonucleotide having a damaged base and deoxyribonucleotide adjacent to the 5' side of the deoxyribonucleotide in DNA strands which contain the damaged base, wherein said enzyme is selected from the group consisting of (a) and (b):
   (a) an enzyme comprising an amino acid sequence having at least 95% sequence identity to the amino acid sequence of SEQ ID NO: 2, and which contains at least one substitution modification relative to the sequence of SEQ ID NO: 2; and
   (b) an enzyme comprising an amino acid sequence having at least 95% sequence identity to the amino acid sequence of SEQ ID NO: 4, and which contains at least one substitution modification relative to the sequence of SEQ ID NO: 4.

2. A recombinant vector containing a DNA encoding an enzyme, wherein the encoded enzyme has an activity of cleaving a phosphodiester bond of deoxyribonucleotide having a damaged base and deoxyribonucleotide adjacent to the 5' side of the deoxyribonucleotide in DNA strands which contain the damaged base, and
   wherein said enzyme is selected from the group consisting of (a) and (b):
   (a) an enzyme comprising an amino acid sequence having at least 95% sequence identity to the amino acid sequence of SEQ ID NO: 2; and
   (b) an enzyme comprising an amino acid sequence having at least 95% sequence identity to the amino acid sequence of SEQ ID NO: 4.

3. The recombinant vector according to claim 2, wherein said enzyme comprises the amino acid sequence of SEQ ID NO: 2 or 4.

4. The recombinant vector according to claim 2, wherein the damaged base is hypoxanthine.

5. The recombinant vector according to claim 2, wherein the damaged base is xanthine.

6. The recombinant vector according to claim 2, wherein the damaged base is uracil.

7. The recombinant vector according to claim 2, wherein the damaged base is abasic.

8. DNA which encodes the enzyme according to claim 1.

9. A recombinant vector containing the DNA according to claim 8.

10. A transformant which is obtained by introducing the recombinant vector according to claim 9 into a host cell.

11. A method of producing an enzyme which has an activity of cleaving a phosphodiester bond of deoxyribonucleotide having a damaged base and deoxyribonucleotide adjacent to the 5' side of the deoxyribonucleotide in DNA strands which contain the damaged base, comprising:
   culturing the transformant according to claim 10 in a medium;
   generating the enzyme and accumulating the same in a culture; and
   collecting the enzyme from the culture.

12. A method of removing a damaged base from a DNA, said method comprising contacting a DNA containing a damaged base with the enzyme according to claim 1 and Endo V, to thereby remove said damaged base from said DNA.

13. A method of removing a damaged base from a DNA, said method comprising contacting a DNA containing a damaged base with the enzyme according to claim 1 and a flap endonuclease, to thereby remove said damaged base from said DNA.

14. The method according to claim 12, wherein the damaged base is at least one selected from a group consisting of hypoxanthine, xanthine, uracil, and abasic.

15. A gene manipulation method comprising:
contacting a DNA containing a damaged base with the enzyme according to claim 1 and Endo V, to cleave said damaged base from said DNA, thereby removing said damaged base from said DNA; and
after the damaged base is removed, ligating the cleaved portions of said DNA through a DNA ligase reaction.

16. The method according to claim 13, wherein the damaged base is at least one selected from a group consisting of hypoxanthine, xanthine, uracil, and abasic.

17. A gene manipulation method comprising:
contacting a DNA containing a damaged base with the enzyme according to claim 1 and a flap endonuclease, to cleave said damaged base from said DNA, thereby removing said damaged base from said DNA; and
after the damaged base is removed, ligating the cleaved portions of said DNA through a DNA ligase reaction.

18. A transformant which is obtained by introducing the recombinant vector according to claim 2 into a host cell.

19. A method of producing an enzyme which has an activity of cleaving a phosphodiester bond of deoxyribonucleotide having a damaged base and deoxyribonucleotide adjacent to the 5' side of the deoxyribonucleotide in DNA strands which contain the damaged base, comprising:
culturing the transformant according to claim 18 in a medium;
generating the enzyme and accumulating the same in a culture; and
collecting the enzyme from the culture.

20. A method of removing a damaged base from a DNA, said method comprising contacting a DNA containing a damaged base with an enzyme which has an activity of cleaving a phosphodiester bond of deoxyribonucleotide having a damaged base and deoxyribonucleotide adjacent to the 5' side of the deoxyribonucleotide in DNA strands which contain the damaged base, and further contacting said DNA with Endo V, to thereby remove said damaged base from said DNA,
wherein said enzyme is selected from the group consisting of (a) and (b):
(a) an enzyme comprising an amino acid sequence having at least 95% sequence identity to the amino acid sequence of SEQ ID NO: 2; and
(b) an enzyme comprising an amino acid sequence having at least 95% sequence identity to the amino acid sequence of SEQ ID NO:4.

21. A method of removing a damaged base from a DNA, said method comprising contacting a DNA containing a damaged base with an enzyme which has an activity of cleaving a phosphodiester bond of deoxyribonucleotide having a damaged base and deoxyribonucleotide adjacent to the 5' side of the deoxyribonucleotide in DNA strands which contain the damaged base, and further contacting said DNA with a flap endonuclease, to thereby remove said damaged base from said DNA,
wherein said enzyme is selected from the group consisting of (a) and (b):
(a) an enzyme comprising an amino acid sequence having at least 95% sequence identity to the amino acid sequence of SEQ ID NO: 2; and
(b) an enzyme comprising an amino acid sequence having at least 95% sequence identity to the amino acid sequence of SEQ ID NO: 4.

22. A gene manipulation method comprising:
contacting a DNA containing a damaged base with an enzyme which has an activity of cleaving a phosphodiester bond of deoxyribonucleotide having a damaged base and deoxyribonucleotide adjacent to the 5' side of the deoxyribonucleotide in DNA strands which contain the damaged base, and further contacting said DNA with Endo V, to thereby remove said damaged base from said DNA; and
after the damaged base is removed, ligating the cleaved portions of said DNA through a DNA ligase reaction,
wherein said enzyme is selected from the group consisting of (a) and (b):
(a) an enzyme comprising an amino acid sequence having at least 95% sequence identity to the amino acid sequence of SEQ ID NO: 2; and
(b) an enzyme comprising an amino acid sequence having at least 95% sequence identity to the amino acid sequence of SEQ ID NO:4.

23. A gene manipulation method comprising:
contacting a DNA containing a damaged base with an enzyme which has an activity of cleaving a phosphodiester bond of deoxyribonucleotide having a damaged base and deoxyribonucleotide adjacent to the 5' side of the deoxyribonucleotide in DNA strands which contain the damaged base, and further contacting said DNA with a flap endonuclease, to thereby remove said damaged base from said DNA; and
after the damaged base is removed, ligating the cleaved portions of said DNA through a DNA ligase reaction,
wherein said enzyme is selected from the group consisting of (a) and (b):
(a) an enzyme comprising an amino acid sequence having at least 95% sequence identity to the amino acid sequence of SEQ ID NO: 2; and
(b) an enzyme comprising an amino acid sequence having at least 95% sequence identity to the amino acid sequence of SEQ ID NO: 4.

* * * * *

SEQUENCE LISTING

```
<160> NUMBER OF SEQ ID NOS: 9

<210> SEQ ID NO 1
<211> LENGTH: 1275
<212> TYPE: DNA
<213> ORGANISM: Pyrococcus furiosus

<400> SEQUENCE: 1
atgatagttg atggagatct tcacattcat tctcactatt ctaaagcagt ttccaagctc      60
atgaccttcc caataattgc tgaaaatgca aaacttaagg gtctcaactt agtagggacg     120
ggggatagtc taaaccctca ctgggaaaag gagttattaa aacactcaaa gcctattgat     180
gatggtactt ttgaagttaa cggggttaag ttcatactaa cctgtgaggt tgaggataaa     240
agaagagttc accatcttct tatattccca acattgtccc aggtgagaga gtttagggag     300
aaagtaaaga tatactccac aaatattgag agtgagggta ggcctaactt aaatttaaca     360
gccgaagaaa ttgctgaaat ggcaaatgag ttagatattt taataggccc cgctcatgcc     420
ttcacacctt ggacaagctt gtataaggaa tatgattcgt tgaaagatgc atatggagat     480
gcgaaaatag attttctgga gttaggactt tcagcggata gtgacatggc tgacatgata     540
aaggctcacc attcaattcc atacttgagc aattccgatg ctcattcccc gaacccccat     600
agattgggaa gggagtttaa cagatttgaa gttaaagatg tgactttga  ggaaattaga     660 aaagcaataa aggggtagg tgggagaaag atcatgttaa atgctggttt agatccaagg     720
cttgggaaat atcatttaac tgcctgcagt aggtgttata caaaatacac acttcaagat     780
gcggtttccc tcagttggaa gtgtcccaag tgtggaggaa ttatcaaaaa ggggtaaga     840 gacagaattc ttgagttggc agatacgagt gaaaaaccaa aagataggcc tccatatgtt     900
aggttagctc ctttggctga gattatagct atggtacttg ggaagggaat tgaaagtaag     960
gctgttaagc ttctatggaa tagattcctt agggaatttg gaagtgaaat aagagtgctg    1020
atagatttgc caatagaatc aatagctagt gttcatgaag gagttgcgaa ggcgatatgg    1080
gcatatagga ataacaaact cattatagtc ccaggagggg gaggtaagta cggagagata    1140
aggatcccag aagaaattct aaaggctaaa attgaagatt tgaatagtat tgagatatcg    1200
ggaggagaag ccgagttgcc gaaacctaag cagaggaccc tgcttcaata tattaaaaat    1260
aaagaggtaa attaa                                                     1275

<210> SEQ ID NO 2
<211> LENGTH: 424
<212> TYPE: PRT
<213> ORGANISM: Pyrococcus furiosus

<400> SEQUENCE: 2

Met Ile Val Asp Gly Asp Leu His Ile His Ser His Tyr Ser Lys Ala
1               5                   10                  15

Val Ser Lys Leu Met Thr Phe Pro Ile Ile Ala Glu Asn Ala Lys Leu
```

```
            20                  25                  30
Lys Gly Leu Asn Leu Val Gly Thr Gly Asp Ser Leu Asn Pro His Trp
            35                  40                  45

Glu Lys Glu Leu Leu Lys His Ser Lys Pro Ile Asp Asp Gly Thr Phe
        50                  55                  60

Glu Val Asn Gly Val Lys Phe Ile Leu Thr Cys Glu Val Glu Asp Lys
65                  70                  75                  80

Arg Arg Val His His Leu Leu Ile Phe Pro Thr Leu Ser Gln Val Arg
                85                  90                  95

Glu Phe Arg Glu Lys Val Lys Ile Tyr Ser Thr Asn Ile Glu Ser Glu
            100                 105                 110

Gly Arg Pro Asn Leu Asn Leu Thr Ala Glu Glu Ile Ala Glu Met Ala
            115                 120                 125

Asn Glu Leu Asp Ile Leu Ile Gly Pro Ala His Ala Phe Thr Pro Trp
        130                 135                 140

Thr Ser Leu Tyr Lys Glu Tyr Asp Ser Leu Lys Asp Ala Tyr Gly Asp
145                 150                 155                 160

Ala Lys Ile Asp Phe Leu Glu Leu Gly Leu Ser Ala Asp Ser Asp Met
                165                 170                 175

Ala Asp Met Ile Lys Ala His His Ser Ile Pro Tyr Leu Ser Asn Ser
            180                 185                 190

Asp Ala His Ser Pro Asn Pro His Arg Leu Gly Arg Glu Phe Asn Arg
            195                 200                 205

Phe Glu Val Lys Asp Val Thr Phe Glu Glu Ile Arg Lys Ala Ile Lys
        210                 215                 220

Gly Val Gly Gly Arg Lys Ile Met Leu Asn Ala Gly Leu Asp Pro Arg
225                 230                 235                 240

Leu Gly Lys Tyr His Leu Thr Ala Cys Ser Arg Cys Tyr Thr Lys Tyr
                245                 250                 255

Thr Leu Gln Asp Ala Val Ser Leu Ser Trp Lys Cys Pro Lys Cys Gly
            260                 265                 270

Gly Ile Ile Lys Lys Gly Val Arg Asp Arg Ile Leu Glu Leu Ala Asp
            275                 280                 285

Thr Ser Glu Lys Pro Lys Asp Arg Pro Pro Tyr Val Arg Leu Ala Pro
        290                 295                 300

Leu Ala Glu Ile Ile Ala Met Val Leu Gly Lys Gly Ile Glu Ser Lys
305                 310                 315                 320

Ala Val Lys Leu Leu Trp Asn Arg Phe Leu Arg Glu Phe Gly Ser Glu
                325                 330                 335

Ile Arg Val Leu Ile Asp Leu Pro Ile Glu Ser Ile Ala Ser Val His
            340                 345                 350

Glu Gly Val Ala Lys Ala Ile Trp Ala Tyr Arg Asn Asn Lys Leu Ile
            355                 360                 365

Ile Val Pro Gly Gly Gly Lys Tyr Gly Glu Ile Arg Ile Pro Glu
        370                 375                 380

Glu Ile Leu Lys Ala Lys Ile Glu Asp Leu Asn Ser Ile Glu Ile Ser
385                 390                 395                 400

Gly Gly Glu Ala Glu Leu Pro Lys Pro Lys Gln Arg Thr Leu Leu Gln
                405                 410                 415

Tyr Ile Lys Asn Lys Glu Val Asn
            420

<210> SEQ ID NO 3
```

```
<211> LENGTH: 1266
<212> TYPE: DNA
<213> ORGANISM: Thermococcus kodakarensis

<400> SEQUENCE: 3
atgatagttg atgccgacct gcacattcat tcgcgctact caaaggctgt ctccaaggca      60
atgactattc caaatctggc cgaaaacgcc cgcttcaagg ggcttgaaat ggttggcacg     120
ggagacatcc tcaacccaaa ctgggagaaa gagcttctca atacacaaa aaaggtagac     180 gaggggacct acgagagaaa cggcatcagg ttcctcctca cgaccgaggt tgaagatacc     240
cgaagggttc accacgtcct tatttttccg aacatcgaaa ccgtccgcga gatgagggag     300
aggcttaagc cttattcttc cgacatcgag agcgagggaa gaccacatct cactctttcg     360
gctgccgaaa tagcggacat tgccaacgag ctcgacgttc tcataggccc agctcacgca     420
tttacacctt ggacaagcct ctacaaggag tatgattcac ttaaggaagc ctacaatgga     480
gcgaaaattc acttcctcga gcttggcctc tcggctgaca gcgagatggc agatatgata     540
aaggcccacc acaaacttac atacctcagc aacagcgacg cccactcacc gatgccccac     600
cggcttggaa gggagttcaa ccgctttgag gttaatgaag ctaccttcga agaaatccgg     660
aaggccatac tgaagcgcgg gagaaagatc gtcctcaacg caggtctcga cccgaggctc     720
ggcaagtacc accttaccgc atgctctcgc tgttacacca gtactccct cgaagaggcc     780 aaagcctttcc gctggaagtg cccaaagtgc ggcgggagaa taaagaaggg cgtgagggac     840
agaatccttg agcttgcaga cactaccgag aggccgaagg acagaccgcc ctacctgcac     900
ctcgcccccc tcgccgagat aatagcgatg gttctcggca aggagtcga gaccaaagct     960 gtaaggcttg tctgggagag atttctgcgg gagttcggaa gcgagataag ggttcttgtt    1020
gacgttcccg tcgaggagct ggcaaaggtt cacgaggagg tagccaaggc agtctgggca    1080
tacagaaagg gcaagctcat cgttatctcc ggcggagggg gcaagtacgg cgagatcaag    1140
ttgccagatg aggtaaggaa tgcgagaatt gaagacctag agaccatcga ggttgaagtt    1200
cccaacgttg aggaaaagcc caagcagagg agcataaccg aattcctccg aaagtcaaat    1260
aagtaa                                                                1266

<210> SEQ ID NO 4
<211> LENGTH: 421
<212> TYPE: PRT
<213> ORGANISM: Thermococcus kodakarensis

<400> SEQUENCE: 4

Met Ile Val Asp Ala Asp Leu His Ile His Ser Arg Tyr Ser Lys Ala
1               5                   10                  15

Val Ser Lys Ala Met Thr Ile Pro Asn Leu Ala Glu Asn Ala Arg Phe
            20                  25                  30

Lys Gly Leu Glu Met Val Gly Thr Gly Asp Ile Leu Asn Pro Asn Trp
        35                  40                  45

Glu Lys Glu Leu Leu Lys Tyr Thr Lys Val Asp Glu Gly Thr Tyr
    50                  55                  60

Glu Arg Asn Gly Ile Arg Phe Leu Leu Thr Thr Glu Val Glu Asp Thr
65                  70                  75                  80

Arg Arg Val His His Val Leu Ile Phe Pro Asn Ile Glu Thr Val Arg
                85                  90                  95

Glu Met Arg Glu Arg Leu Lys Pro Tyr Ser Ser Asp Ile Glu Ser Glu
            100                 105                 110
```

Gly Arg Pro His Leu Thr Leu Ser Ala Ala Glu Ile Ala Asp Ile Ala
            115                 120                 125

Asn Glu Leu Asp Val Leu Ile Gly Pro Ala His Ala Phe Thr Pro Trp
        130                 135                 140

Thr Ser Leu Tyr Lys Glu Tyr Asp Ser Leu Lys Glu Ala Tyr Asn Gly
145                 150                 155                 160

Ala Lys Ile His Phe Leu Glu Leu Gly Leu Ser Ala Asp Ser Glu Met
                165                 170                 175

Ala Asp Met Ile Lys Ala His His Lys Leu Thr Tyr Leu Ser Asn Ser
            180                 185                 190

Asp Ala His Ser Pro Met Pro His Arg Leu Gly Arg Glu Phe Asn Arg
        195                 200                 205

Phe Glu Val Asn Glu Ala Thr Phe Glu Glu Ile Arg Lys Ala Ile Leu
    210                 215                 220

Lys Arg Gly Arg Lys Ile Val Leu Asn Ala Gly Leu Asp Pro Arg Leu
225                 230                 235                 240

Gly Lys Tyr His Leu Thr Ala Cys Ser Arg Cys Tyr Thr Lys Tyr Ser
                245                 250                 255

Leu Glu Glu Ala Lys Ala Phe Arg Trp Lys Cys Pro Lys Cys Gly Gly
            260                 265                 270

Arg Ile Lys Lys Gly Val Arg Asp Arg Ile Leu Glu Leu Ala Asp Thr
        275                 280                 285

Thr Glu Arg Pro Lys Asp Arg Pro Pro Tyr Leu His Leu Ala Pro Leu
    290                 295                 300

Ala Glu Ile Ile Ala Met Val Leu Gly Lys Gly Val Glu Thr Lys Ala
305                 310                 315                 320

Val Arg Leu Val Trp Glu Arg Phe Leu Arg Glu Phe Gly Ser Glu Ile
                325                 330                 335

Arg Val Leu Val Asp Val Pro Val Glu Glu Leu Ala Lys Val His Glu
        340                 345                 350

Glu Val Ala Lys Ala Val Trp Ala Tyr Arg Lys Gly Lys Leu Ile Val
    355                 360                 365

Ile Ser Gly Gly Gly Lys Tyr Gly Glu Ile Lys Leu Pro Asp Glu
370                 375                 380

Val Arg Asn Ala Arg Ile Glu Asp Leu Glu Thr Ile Glu Val Glu Val
385                 390                 395                 400

Pro Asn Val Glu Glu Lys Pro Lys Gln Arg Ser Ile Thr Glu Phe Leu
                405                 410                 415

Arg Lys Ser Asn Lys
            420

<210> SEQ ID NO 5
<211> LENGTH: 45
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (25)..(25)
<223> OTHER INFORMATION: n is a, c, g, or t

<400> SEQUENCE: 5
cgaactgcct ggaatcctga cgacntgtag cgaacgatca cctca                45

<210> SEQ ID NO 6
<211> LENGTH: 45

```
<212> TYPE: DNA
<213> ORGANISM: Artificial Sequence
<220> FEATURE:
<223> OTHER INFORMATION: Synthetic oligonucleotide

<400> SEQUENCE: 6
tgaggtgatc gttcgctaca tgtcgtcagg attccaggca gttcg          45

<210> SEQ ID NO 7
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 7
cgaactgcct ggaatcctga cgacatgtag cgaacgatca cctca          45

<210> SEQ ID NO 8
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 8
gggccatggt agttgatggc gatctgcaca                           30

<210> SEQ ID NO 9
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 9
ggggcggccg cttaatttac ctctttattt ttaatatatt gaagc          45
```